United States Patent [19]

Last

[11] Patent Number: 4,905,997
[45] Date of Patent: Mar. 6, 1990

[54] HEAT POD BODY MUSCLE TREATMENT DEVICE

[75] Inventor: Anthony J. Last, Oakville, Canada

[73] Assignee: Rainbow Star Licensing, Fribourg, Switzerland

[21] Appl. No.: 291,114

[22] Filed: Dec. 28, 1988

Related U.S. Application Data

[63] Continuation of Ser. No. 719,986, Apr. 4, 1985, Pat. No. 4,832,031, which is a continuation-in-part of Ser. No. 247,258, Mar. 25, 1981, Pat. No. 4,509,750.

[30] Foreign Application Priority Data

Apr. 9, 1980 [GB] United Kingdom ............... 8011688

[51] Int. Cl.⁴ ............................................. A63B 69/38
[52] U.S. Cl. ................................... 273/29 A; 128/402
[58] Field of Search ...................... 273/26 R, 29 A; 128/402, 77, 25 R, 80 C, 166, DIG. 20, 403; 604/219, 113, 114

[56] References Cited

U.S. PATENT DOCUMENTS

| | | | |
|---|---|---|---|
| 1,549,510 | 8/1925 | Schnitzler | 128/DIG. 20 |
| 2,467,447 | 4/1949 | Strezoff | 219/313 |
| 2,749,914 | 6/1956 | Barley | 128/402 |
| 2,909,176 | 10/1959 | Ashe | 128/402 |
| 2,911,974 | 11/1959 | Spence | 128/402 |
| 3,149,943 | 9/1964 | Amador | 128/402 |
| 3,186,404 | 6/1965 | Gardner | 128/402 |
| 3,212,497 | 10/1965 | Dickinson | 128/DIG. 20 |
| 3,506,013 | 4/1970 | Zdenek | 128/402 |
| 3,548,819 | 5/1970 | Davis et al. | 128/402 |
| 3,561,435 | 2/1971 | Nicholson | 128/402 |
| 3,785,375 | 1/1974 | Lipson | 128/DIG. 20 |
| 4,044,773 | 8/1977 | Baldwin | 128/402 |
| 4,107,509 | 8/1978 | Sher et al. | 128/402 |
| 4,344,303 | 8/1982 | Kelly Jr. | 128/402 |
| 4,530,220 | 7/1985 | Nambu et al. | 128/402 |

*Primary Examiner*—T. Brown
*Attorney, Agent, or Firm*—ROsen, Dainow & Jacobs

[57] ABSTRACT

A method for the prevention of and the treatment for epicondylalgia externa, popularly known as tennis elbow, is disclosed. The method involves the absorption and dissipation of the vibrational shocks caused by the off-centre hitting of a tennis ball during pronation and supination of the wrist by use of a vibration absorbing pad fluid containing device covering either the extensor or flexor muscles of the forearm. The pad is shaped to conform with the extensor of flexor muscle in the forearm, is filled with a viscous fluid or semi-fluid which will flow enough to maintain a close contact with the muscle from wrist to elbow. The viscous fluid has a thermal conductivity of less than 0.1 W/(m.° C.).

3 Claims, 1 Drawing Sheet

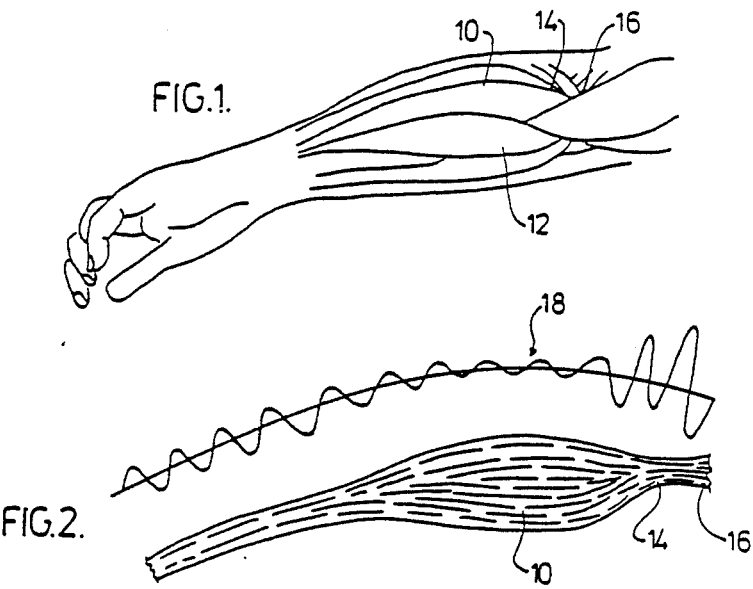
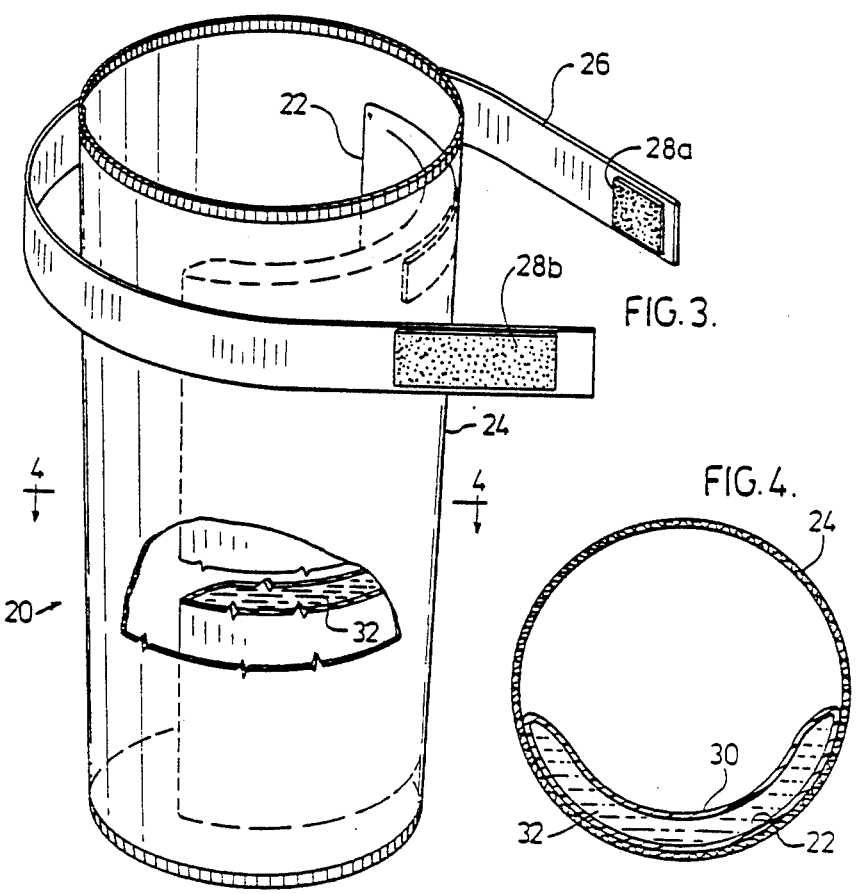

HEAT POD BODY MUSCLE TREATMENT DEVICE

REFERENCE TO RELATED APPLICATION

This application is a continuation of pending application Ser. No. 719,986, filed Apr. 4, 1985 (now U.S. Pat. No. 4,832,031), which is a continuation-in-part of application Ser. No. 247,258, filed Mar. 25, 1981, now U.S. Pat. No. 4,509,750, issued Apr. 9, 1985.

FIELD OF INVENTION

The present invention relates to a vibration absorbing pad for use in connection with racquet and ball game playing and to a passive heating pad for therapeutic application.

BACKGROUND TO THE INVENTION

The increased playing of tennis, squash and racquetball by men and women over 30 years of age has led to the increase of a painful problem known as "tennis elbow". This condition usually occurs in people between 30 and 50 years of age, where muscles and tendons have become less supple and less able to absorb and dissipate vibrational shocks.

Epicondylalgia externa (tennis elbow) is not only found in racquet sports but can be aggravated by other pursuits, such as, golf and bowling. It can also be found in certain trades, such as carpentry, due to repeated hammering and driving of screws, and in house painting, due to the forward and backward stroke of the brush. Also, it can be found in industrial jobs involving pneumatic hammers and the like.

The motive power that enables the forearm to be rotated from side to side comes from the wrist and not the elbow. Therefore, the start of the problem is at the wrist during pronation and supination. Shock and/or vibration occurring at the wrist is propagated up the extensor muscles until it terminates in the outer and supporting parts of the attachment to the head of the humerus called the lateral epicondyle and also the extensor tendon that attaches the forearm extensor muscles to the epicondyle. The vibration can also be propagated up the flexor muscles in the same manner.

The forearm extensor muscles are those that come into play during the extension, raising or snapping of the wrist. Every time a tennis ball hits a racquet there is a certain force propagated up the forearm muscles which are already in tension due to the weight and acceleration of the racquet and the tension caused by the centrifugal force of the stroke If the ball is mis-hit, an extra force is added which leads to an upward snap of the wrist. It is this extra stress that travels up the extensor muscles to the epicondyle and causes the trauma leading to inflammation. To some extent, aluminum metal or graphite racquets tend to reduce the stress because of their light weight and also racquets with oversized heads tend to reduce the problem because the larger area that the ball can hit, without twisting the racquet, reduces the number of mis-hits.

Prior art procedures to control epicondylalgia externa include tension bandages for support and non-elastic bandages which are fastened around the forearm to inhibit the massive movement of the extensor and flexor muscles and so absorb much of the shock. Further, both wrist and forearm straps which are joined by a piece of spring metal and situated either on the top or bottom of the forearm have been used. This spring metal absorbs some of the massive shock occurring in the muscles but does not absorb the surface vibrations that do much of the damage and inhibit healing of the elbow.

In the parent application, the following U.S. patents have been cited as prior art and are made of record herein: U.S. Pat. Nos. 3,631,854, 3,561,435, 2,245,909, 2,943,859, 3,831,467, 3,900,035, 3,678,936, 2,749,914, 3,506,013, 4,116,236, 3,703,171, 4,204,543, 3,736,769, 4,044,773 and 3,149,943. These references relate generally to a variety of structures which are applied to various body parts and, as will become apparent from the discussions below, are not relevant to the present invention.

The use of heat as therapy for muscles or a group of muscles in the human body is a well-known technique. Prior art thermal pads employ some form of positive or external heating means, for example, electricity, chemical means, or steam or hot water. Typical prior art in this area are the following U.S. Pat. Nos.: 2,911,974, 2,909,176, 2,595,328, 3,463,161 and 3,901,225. As will become apparent from the discussion below, this prior art is not relevant to the present invention.

SUMMARY OF INVENTION

The present invention relates to the control of epicondylalgia externa in a manner superior to the prior art. In the present invention, a pad containing a highly viscous vibration-absorbing fluid is maintained in close contact with the skin adjacent the extensor or flexor muscles. The pad may be maintained in position by means of an elastic tube or sleeve. An elastic strap which can be tightened by Velcro fasteners or the like around the widest part of the forearm is provided to ensure close contact with the aforementioned muscles and the integrity of the device on the arm during violent exercise.

Accordingly, this invention provides a device for controlling epicondylalgia externa in a person to minimize the incidence thereof or relieve the symptoms thereof, which comprises pad means containing vibration-absorbing high viscosity permanently-fluid material, the pad means being dimensioned to extend over an area of the forearm of a wearer of the device which is at least half of the area extensor or flexor muscles in the forearm projected to the .forearm surface, and means for maintaining the pad means in contact with the forearm, thereby to dampen and absorb surface vibrations in the extensor and flexor muscles and minimize traumatization and consequent inflammation of the of the epicondyle of the forearm.

The device of this invention also may be used on other parts of the human frame where vibration can cause similar problems. An example is the occasional pain occurring in the lower leg, due to the vibration experienced by jogging on hard pavements.

This invention further provides a method of absorbing surface vibrations along body muscles tending to traumatize portions thereof. A pad of vibration-absorbing high viscosity permanently-fluid material is applied to the body muscle substantially along the whole length thereof during periods of activity when the surface vibrations are induced. In this way, the surface vibrations are dampened and absorbed and the trauma produced thereby is decreased.

In one embodiment of the invention, there is provided a passive heating pad for application to the body of an animal, including man, for the heat treatment of a muscle or group of muscles, for example, in the treatment of arthritis, comprising at least one envelope containing a highly viscous liquid having a low thermal conductivity.

BRIEF DESCRIPTION OF DRAWINGS

FIG. 1 is a cut-away section of a forearm showing the extensor and flexor muscles and epicondyle;

FIG. 2 is a drawing of one of the extensor muscles showing the muscle, ligament and epicondyle and the amplitude of surface vibrations occurring in the muscle;

FIG. 3 is a perspective view of a device provided in accordance with a preferred embodiment of the invention; and FIG. 4 is a cross-sectional view of the vibration absorbing pad of the invention at the line A—A shown in FIG. 3.

GENERAL DESCRIPTION OF INVENTION

As mentioned above, the inventor has discovered that the incidence of epicondylalgia externa arises from vibrations passing along the extensor and flexor muscles of the forearm. The present invention seeks to overcome this problem by applying a pad of vibration absorbing material to the forearm.

Essential to this embodiment of the invention is the use of a vibration-absorbing material of high viscosity in the range of about 100,000 to about 1,000,000 SUS units at 100° F. Vibration is essentially a pressure wave passing through a material. In liquids, adjacent molecules contact one another so as to propogate a wave motion through the liquid. If the molecules find it harder to move, then the vibrational energy is absorbed and degrades into heat through friction. High viscosity is one manner of inhibiting molecule motion and small solid particles alone aid in the absorption of energy. In the present invention, a vibration-absorbing material is employed in contact with body parts.

As discussed earlier, there have been a variety of proposals to provide various structures for the application to body parts, but none has recognized that a pad of vibration-absorbing material may be used for the control of tennis elbow.

For example, U.S. Pat. No. 3,631,854 describes an inflatable surgical cast which is inflated by the introduction of a liquid-curable resin composition, such as a foamable polyurethane prepolymer composition, into the space between the inner and outer walls. The liquid composition then is cured to a rigid foam. While some liquid curable resin compositions having the required viscosity values, are vibration-absorbing materials and useful in this invention, such resin materials remain uncured when used herein, in contrast to this prior art. The vibration-absorbing material used in this invention is permanently fluid, usually liquid or possessing a continuous liquid phase, although the viscosity of the liquid composition usually changes during use, as described below.

U.S. Pat. No. 3,561,435 describes a combined splint and container. The container is filled with water or ice. Neither of these materials is effective in absorbing vibrations, so that the structure described in this prior art would not be useful in controlling tennis elbow.

U.S. Pat. No. 2,245,909 describes a cast which has a fillable chamber into which may be introduced a fluid. Air and hot or cold water are the only materials mentioned. As in the case of U.S. Pat. No. 3,561,435, none of the materials mentioned is vibration absorbing, so that the structure described is not effective in controlling tennis elbow.

U.S. Pat. No. 2,943,859 describes an arm stiffening device which slips over the elbow of a golfer and is inflated with air. Since air is not vibration absorbing, this device is not useful for controlling tennis elbow.

U.S. Pat. No. 3,831,467 describes a knee brace which includes a resilient but solid pad. A similar structure is described in U.S. Pat. No. 4,116,236. Since the resilient pad resists conforming to the shape of the user's forearm, the described structures are ineffective in controlling tennis elbow.

U.S. Pat. No. 3,900,035 describes a therapeutic elastic bandage having spaced transverse pockets into which elastic and flexible bags are inserted. The bags may be filled with antifreeze solution or with sand, depending on the intended use. Neither material is vibration absorbant and hence the structure is not useful in controlling tennis elbow.

U.S. Pat. No. 3,678,936 describes an ice bag for the treatment of athletes which includes a hollow jacket for holding crushed ice. Like water, ice is not a vibration absorbing material and hence is not suitable for the purposes of this invention.

U.S. Pat. No. 2,749,914 describes a thermal pack for body application comprising a wrapper sheet and liquid cell units which contain a heat storage liquid, with water and diethylene glycol being mentioned. Neither material is vibration absorbent and hence is not useful for the purposes of the present invention.

U.S. Pat. No. 3,506,013 describes an iced dressing. A structure for application to an arm is illustrated. However, the compartment of the dressing contains ice, which is not vibration absorbent. In any event, the rigid structure would be unsuitable for the purposes of this invention.

U.S. Pat. No. 4,204,543 describes a coolant band comprising a band of textile material containing a pocket with an opening for receiving and storing a bag of freezable liquid or semi-liquid material. The materials specifically described are not vibration absorbent and hence are not useful in the present invention.

U.S. Pat. Nos. 3,736,769, 4,044,773 and 3,149,943 describe cooling devices wherein liquid is contained in a pocket and frozen. Again, the materials used are not vibration absorbing and hence the devices described are not useful in controlling tennis elbow.

As will be seen from the above discussion, none of the many devices described in the prior art is suitable for use in the control of tennis elbow. As far as the applicant is aware, there is no prior art which is specifically directed to the control of tennis elbow by the use of a pad of vibration-absorbing high viscosity permanently-fluid material, nor is there any prior art suggestion to provide therapeutic devices which might incidentally be useful in the control of tennis elbow.

Any material which is vibration-absorbing, of high viscosity and permanently-fluid may be used in this invention. Generally, the material also may have the viscosity of putty, and preferably is of low thermal conductivity. The material may also be of a material which has a decreasing viscosity with increasing temperature. In general, the vibration-absorbing material has a viscosity in the range of about 100,000 to about 1,000,000 SUS units at 100° F.

In one preferred embodiment of the invention, the high viscosity absorbant material comprises a three-component system comprising a liquid polybutene, a petroleum wax and a solid filler material. In this composition, the polybutene component acts as a high viscosity matrix material, and the petroleum wax acts as a skeleton around which the polybutene flows.

Polybutene is available in a variety of grades and molecular weights from various manufacturers. A liquid polybutene having a number average molecular weight in the range of about 1,000 to about 1,500 is preferred. One such polybutene is that available from Ashland Chemicals under the trademark "Petrofin 300", which has a number average molecular weight of 1390. Polybutenes usually have a high viscosity at body heat temperatures but a much lower viscosity at higher values.

The presence of the petroleum wax and the solid filler material in the composition increases the stiffness of the mixture to provide a higher viscosity value, within the viscosity range of about 100,000 to about 1,000,000 SUS units at 100° F. (i.e. approximately body heat temperature).

The solid filler material may be a finely-divided inert solid, such as calcium carbonate, sawdust or powdered rubber.

When the material has a low thermal conductivity, the pad may also function as a passive heating pad for the therapeutic application of heat to a body muscle or group of muscles requiring treatment, for example, in the treatment of arthritis. While mainly useful for man, the passive heating pad may be used with other animals, such as horses.

In this embodiment of the invention, the passive heating pad comprises an envelope or a plurality of envelopes made from a plastic material which is impermeable to water and which can be heat sealed. The envelope or envelopes contain a viscous composition which has a low thermal conductivity of less than 0.1 W/(m.°C.). The viscosity of the composition should be such that the composition is comparatively stiff when cold or cool but flows easily when blood heat is reached. Usually, the composition has a viscosity in the range of about 100,000 to about 1,000,000 SUS units at 100° F. (approximately body heat temperature). The pad also may be made of a plastic envelope into which is placed a rubber or rubber-like formulation, which has a low thermal conductivity, and which can be cut to fit the envelope.

In use, the passive heating pad is placed over the muscle, muscle group or joint where relief is required and is held there by a bandage, which may be a normal bandage or a tensor bandage. The skin below the pad commences to heat up, since the normal radiation of heat from the skin is inhibited by the pad. If the muscle or muscle group is exercised, the heat release is increased until perspiration commences.

The evaporation of the perspiration is inhibited as it is beneath the pad and the pad is in contact engagement with the skin and, therefore, the muscle or group below the pad increases in temperature. In order to maximize this effect, the pad moulds itself closely to the skin surface to inhibit the evaporation of the perspiration.

Increased heat in the muscles has the effect of increasing the blood flow, not only in the area under the pad, but also in adjacent areas. Increased blood flow has a salutary and healing effect on numerous minor injuries which can occur in the human frame, either at work or at play.

Essential to this embodiment of the invention is the use of a material having a low thermal conductivity of less than 0.1 W/(m.°C.). If the thermal conductivity is higher, more heat is lost through the pad by the muscle or muscle group that is being covered by it and the muscles do not heat up fast enough for the protection from injury or healing effect on muscles or joints that the increased blood flow accords. The thermal conductivity value of less than 0.1 W/(m.°C.) used herein is a lot lower than that of many common materials, such as water (0.594 W/(m.°C.)), ethylene or propylene glycol and their mixtures with water (greater than 0.265 W/(m.°C.)), Vaseline (0.183 W/(m.°C.)), sand (0.33 W/(m.°C.)), glycerol (0.284 W/(m.°C.)), and natural rubber (0.138 W/(m.°C.)). None of these materials, therefore, is suitable for use in a passive heating pad.

In a preferred embodiment of the heating pad, the filler material preferably is formulated so as to generate some heat by internal friction, such as by the utilization of fine solids, for example, sawdust or powdered rubber, dispersed in a viscous medium.

The passive heating pad of the invention is distinguished from the prior art in providing passive heat therapy, while in the prior art some form of external heat needs to be applied to a medium to be effective. There have, however, been a few attempts at providing a passive heating pad but none has the utility of the pad of this invention.

For example, U.S. Pat. No. 2,911,974 describes a device which surrounds an entire body member and elastic means is used to maintain and seal the bag to the limb. The bag has no insulating qualities in itself and external insulation is provided to maintain heat localized. The described structure cannot be adapted to cover a single muscle or group of muscles.

Similarly, in U.S. Pat. No. 2,909,176, there is described a pad structure comprising a fabric lining and insulating batting which is arranged about an entire body member. Again, the structure cannot be adapted to cover a single muscle or group of muscles.

Further, in the case of both these patents, the structure is not able to absorb heat, so that upon ceasing exercising and working, the heat pad loses its heat very quickly to the ambient air. As a result of the use of low conductivity material in the present invention, heat is stored and available to continue heating the muscle or group of muscles once the exercise has finished.

U.S. Pat. No. 3,901,225 describes the use of an air bladder to force a therapeutic pad into pressure contact with an injured area. There are no specific materials specified for the therapeutic pad but it is clear that, for heating purposes, the materials are pre-heated.

U.S. Pat. No. 3,900,035 has been described above. The use of sand as a heat-retaining material in a therapeutic elastic bandage is described. However, the sand is preheated and, in any event, has a thermal conductivity well above the maximum value used in the passive heating pad of the invention.

U.S. Pat. No. 3,463,161 describes a heating pad which is described as including a heat maintaining composition. The material is preheated to the required temperature prior to application to the required treatment area. The materials described as suitable in this prior art have thermal conductivites well above the maximum value of 0.1 W/(m.°C.) used herein.

U.S. Pat. No. 2,595,328 describes a hot pack type of material. This prior art mentions, as filler materials, aqueous solutions of alcohol, glycerol and ethylene glycol, as well as gases and small solid particles, such as sand, ground cork, soapstone, resilient rubber, diatomaceous earth or mixtures of the same. Ground cork and diatomaceous earth have thermal conductivities of less than 0.1 W/(m.°C.) as indeed do most gases. However, since they are used as small particles in an air medium, heat can leak readily through the device and the heat retention capability of the heating pad of the invention is not readily achieved.

In one aspect of the heating pad embodiment of the invention, the envelope material may be constructed of heat-sealable nylon material or any other impervious plastic material which is heat sealable and inert to living matter. The envelope is filled with the filler material and a plurality of envelopes may be arranged in a sheet with tear lines surrounding each, so that a pad of any desired size comprising a single or a multiple number of envelopes may be provided.

DESCRIPTION OF PREFERRED EMBODIMENTS

Referring now to the drawings, and in particular to FIGS. 1 and 2, wherein there is illustrated the problem to which the invention relates. In FIG. 1, the numeral 10 designates the extensor group of muscles and numeral 12 the flexor group of muscles of a person's forearm. Numerals 14 and 16 designate the extensor tendon and epicondyle respectively of the extensor muscle.

In FIG. 2, only one extensor muscle 10 is shown. As in FIG. 1, numerals 14 and 16 designate the extensor tendon and epicondyle. Numeral 18 shows the amplitude of the surface vibrations as they leave the wrist area and proceed along the extensor muscles 10. They will be at their lowest amplitude at the largest cross-sectional area and, as the extensor muscle 10 necks down, so the vibration increases in amplitude to a maximum at the termination point, the epicondyle 16.

The propagation of the vibrations along the muscles is maintained until the muscle absorbs the energy and dissipates it throughout its length as heat. The muscle is itself shaped in such a way that any small vibration on its diameter rapidly increases in amplitude as the diameter becomes smaller. Those versed in the art of transmission line theory will recognize this fact and they will also recognize that, if conditions of resonance are present, the amplitudes of vibrations may become even higher. At the point where the muscle tendon 14 joins the epicondyle 16 there is an impedance change which becomes even greater at the attachment to the bone. This impedance change, which can be defined as a change in the ability to conduct or absorb vibrations, means that the energy must be released in the form of heat or strain on the epicondyle 16. It is the latter that causes the small surface tears and lesions leading to the inflammation of the epicondyle 16 and surrounding tissue.

In the present invention, the surface vibrations along the extensor muscles are absorbed and thereby reduces the trauma at the epicondyle 16. The application of a pad of viscous vibration-absorbing permanently-fluid material to the forearm increases the temperature in the muscle below the pad. The temperature increase is due to the inability of the perspiration at the skin surface to evaporate and to the friction and heat insulation of the pad itself. This increase in temperature is beneficial in that it leads to a greater absorption of vibrational energy. F. Dunn, in the Journal of the Acoustical Society of America, Volume 34, page 1545, in 1962, showed that the absorption coefficient of a vibration of 1 MHz in many types of biological tissue increases with increasing temperature.

Turning now to FIGS. 3 and 4, wherein there is illustrated a preferred embodiment of a vibration-absorbing device of the invention useful in the control of tennis elbow, a device 20 comprises a vibration absorbent pad 22 filled with viscous vibrating-absorbing permanently-fluid material, which is attached by means of a fastener 23, Velcro or the like, to the inside of an elastic tube 24, which is shaped and sized to be fitted on the forearm of the user of the device 20 from the wrist to just below the joint of the elbow The pad 22 extends for almost the whole length of the tube 24. The tube may be constructed of any convenient elastic material, such as, flexible woven or knitted elastic material, or a one-way stretch material which stretches circumferentially of the tube. Over the tube 24 at approximately the widest diameter of the forearm, an elastic strap 26 is attached at one end thereof (shown detached in the drawing) and surrounds the forearm and places extra tension on the pad 22 to prevent movement thereof during violent movement of the forearm on which the device 20 is worn. The strap 26 is fastened to itself by any suitable means, such as Velcro fasteners 28a and 28b or buttons.

As may be seen from the cross-sectional view of FIG. 4, the pad 22 is a flat or slightly curved container 30, made from any suitable material, such as, heat-sealable nylon, conforming with the extensor (or flexor) muscle and extends from just above the wrist to just below the elbow. The container 30 is filled with a viscous material having a continuous liquid phase 32 which will absorb vibrations. The viscous liquid must be able to flow, so as to maintain contact with the muscles as they flex with forearm motion. The viscous liquid has a viscosity of about 100,000 to about 1,000,000 SUS units at 100° F. The liquid phase may comprise a liquid polybutene having a number average molecular weight of about 1,000 to 1,500 or may comprise an uncured thermal setting glue or a silicone fluid. Preferably, the material has a low thermal conductivity of less than about 0.1 W/(m.°C.).

The device 20 may be positioned on a user's forearm with the pad 22 inside the forearm adjacent to the flexor muscles, or outside adjacent to the extensor muscles. Sufferers from tennis elbow may wear the pad during normal everyday activity. The pad 22 effectively absorbs small vibrations that tend to increase additively the inflammation of the epicondyle due to small actions, such as, lifting objects and even the action of writing. In this way, the inflamed area can get a more complete rest than is normally possible and this leads to a relief of the symptoms and pain of epicondylalgia externa. The device 20 should always be worn when heavy exercise of the arm is contemplated.

EXAMPLE

To test the suitability of materials for use as the vibration-absorbing liquid in this invention, comparative tests were performed to ascertain the ability of the materials to absorb high frequency sound waves. The sound wave pattern was considered equivalent to the wave form of the vibrations encountered along the extensor muscle.

Distilled and deionized water was used as a reference standard and its attenuation of 2.25 MHz pulses over a distance of 0.5 inches is essentially zero dB. The following Table I indicates the results obtained.

TABLE I

| Material | dB Attenuation | Rates of Attenuation |
| --- | --- | --- |
| Water | 0 | 1:1 |
| Glycerine | 2 dB in | 1:1.25 |
| Soya Bean Oil | 2 db out | 1.25:1 |
| Rubber composition[1] | 42 db out | 125:1 |
| LASTRAP formulation I[2] | 56 dB out | 630:1 |
| LASTRAP formulation II[3] | 76 dB out | 6300:1 |

Notes:
[1]Hot melt adhesive HM 1500 - H.B. Fuller Co.
[2]Polybutene, petroleum wax and 35 wt. % $CaCO_3$
[3]Polybutene, petroleum wax and 40 wt. % $CaCO_3$ The results were obtained in the following way. A piezo-electric receiver and transmitter of the 2.25 MHz pulses were placed opposite each other in a holder into which could be poured the material to be measured. The transmitter/receiver used to operate the transducers was a Branson Sonoray 600 series. This unit is an instrument using ultrasound for non-destructive testing and thickness gauging of solid materials and the 600 unit is equipped with attenuators in the receiver portion of the circuit. When the attenuation dB IN/OUT attenuators are in the OUT position, the maximum gain of the received signals from the test object is obtained. The gain (amplitude) of the received signals is decreased in fixed increments as each toggle switch is placed in the IN position. The total range provided by these controls is 62 dB, which permits comparison of the amplitudes of signals with ratios in excess of 1250 to 1.

Such comparisons were achieved in the test work by setting the signal from the reference material (water) at a convenient screen level (50% of the screen height) by adjustment of the GAIN control with all the attenuators in the IN position, which then became the "reference" amplitude signal.

For the unknown, the signal was increased in 2 dB steps by switching combinations of the dB controls to the OUT position until the amplitude of the unknown signal reaches the same amplitude as the reference signal. Of the materials tested, glycerihe and soya bean oil had somewhat similar absorption characteristics to water while the uncured rubber and the LASTRAP formulations, all used in this invention, had significant vibration-absorbing capability.

SUMMARY OF DISCLOSURE

In summary of this disclosure, the present invention relates to the relief of tennis elbow by the use of a novel device. Other modifications may be made within the scope of the invention.

What I claim is:

1. A method of treatment of body muscles, which comprises:
    applying to the surface of the body skin adjacent the muscle, group of muscles of joint to be treated, a flexible pad comprising at least one moisture-impervious envelope containing highly viscous permanently-fluid material having a thermal conductivity less than about 0.1 W/(m.°C.),
    causing heat to be generated by the muscle, group of muscles or joint and preventing the heat from being dissipated by the skin in the area of the pad, so that the retained heat induces therapeutic action on said muscle, group of muscles or joint, and
    absorbing heat in said highly viscous material, whereby the flexible pad may continue to heat the muscle, group of muscles or joint after the activity causing heat to be generated thereby ceases.

2. The method of claim 1 wherein said highly viscous material comprises a continuous liquid phase and finely-divided solid material dispersed in said liquid phase.

3. The method of claim 7 wherein said highly viscous material has a viscosity in the range of about 100,000 to about 1,000,000 SUS units at 100° F.

\* \* \* \* \*